United States Patent [19]

Van Lommen et al.

[11] Patent Number: 5,801,179

[45] Date of Patent: Sep. 1, 1998

[54] VASOCONSTRICTIVE SUBSTITUTED ARYLOXYALKYL DIAMINES

[75] Inventors: Guy Rosalia Eugène Van Lommen, Berlaar; Marcel Frans Leopold De Bruyn, Wortel; Piet Tom Bert Paul Wigerinck, Turnhout, all of Belgium

[73] Assignee: Janssen Pharmaceutica, NV, Beerse, Belgium

[21] Appl. No.: 867,870

[22] Filed: Jun. 2, 1997

Related U.S. Application Data

[62] Division of Ser. No. 612,849, filed as PCT/EP94/02702 Aug. 12, 1994, Pat. No. 5,677,310.

[30] Foreign Application Priority Data

Aug. 19, 1993 [EP] European Pat. Off. ............ 93.202.44.8
Aug. 19, 1993 [EP] European Pat. Off. ............ 93.202.444.1

[51] Int. Cl.$^6$ .................... A61K 31/155; C07C 279/30; C07D 239/14; C07D 239/42

[52] U.S. Cl. .................. 514/255; 514/227.5; 514/230.5; 514/311; 514/634; 544/105; 544/402; 546/178; 546/246; 548/217; 548/491; 548/503; 548/569; 549/15; 549/362; 549/400; 549/401; 549/408; 549/462; 549/366; 564/104; 564/230; 564/240; 564/241

[58] Field of Search ................. 514/255, 227.5, 514/230.5, 311, 634; 564/104, 230, 240, 241; 544/105, 402; 546/178, 246; 548/217, 491, 503, 569; 549/15, 362, 400, 401, 408, 462, 366

[56] References Cited

U.S. PATENT DOCUMENTS

| | | | |
|---|---|---|---|
| 4,438,128 | 3/1984 | Wiedemann et al. | 424/273 |
| 4,593,039 | 6/1986 | Baldwin et al. | 514/362 |
| 5,229,392 | 7/1993 | George et al. | 514/275 |
| 5,399,581 | 3/1995 | Laragh | 514/396 |
| 5,548,061 | 8/1996 | Masaki et al. | 530/324 |

FOREIGN PATENT DOCUMENTS

| | | |
|---|---|---|
| A0 042 593 | 12/1981 | European Pat. Off. |
| A0 511 072 | 10/1992 | European Pat. Off. |
| 0594484 | 4/1994 | European Pat. Off. |

OTHER PUBLICATIONS

O'Connor, Adrenal Medulla, Cecil Textbook of Medicine, 20th Edition, vol. 2, pp. 1253–1257, 1996.

Posner, Disorders of Sensation, Cecil Textbook of Medicine, 20th Edition, vol. 2, pp. 2030–2032, 1996.

Benkert et al., Relations between structure and the nonadrenaline depleting effects of guanidine and amidine derivatives, Arzneim. Forsch., 25(9), pp. 1404–1408, 1975.

Benkert et al., Arzneimittel Forschung. Drug Research, vol. 25, No. 9, 1975, pp. 1404–1408.

*Primary Examiner*—Mukund J. Shah
*Assistant Examiner*—Deepak R. Rao
*Attorney, Agent, or Firm*—Ellen Ciambrone Coletti

[57] ABSTRACT

The present invention is concerned with compounds having the formula

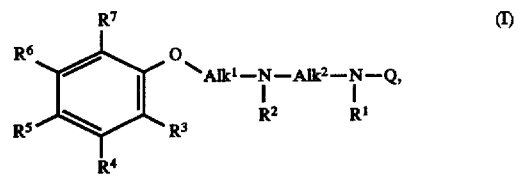

the pharmaceutically acceptable acid addition salts thereof, and the stereochemically isomeric forms thereof, wherein $R^1$ is hydrogen or $C_{1-6}$alkyl; $R^2$ is hydrogen or $C_{1-6}$alkyl; $R^3$ is $C_{1-6}$alkyl, hydroxy, cyano, halo, $C_{1-6}$alkyloxy, aryloxy, arylmethoxy, $C_{2-6}$alkenyl, $C_{2-6}$alkynyl, $C_{1-6}$alkyl—S—, $C_{1-6}$alkyl(S=O)—, $C_{1-6}$alkylcarbonyl; $R^4$ is hydrogen, halo, hydroxy, $C_{1-6}$alkyl, or $C_{1-6}$alkyloxy; or $R^3$ and $R^4$ taken together form a bivalent radical; $R^5$ and $R^6$ each independently are hydrogen, halo, hydroxy, $C_{1-6}$alkyl, $C_{1-6}$alkyloxy, aryloxy or arylmethoxy; $R^7$ is hydrogen; Alk$^1$ is $C_{2-5}$alkanediyl; Alk$^2$ is $C_{2-15}$alkanediyl; Q is a heterocyclic ring containing at least one nitrogen atom or a radical of formula

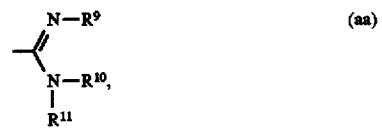

Pharmaceutical compositions, preparations and use as a medicine are described.

10 Claims, No Drawings

VASOCONSTRICTIVE SUBSTITUTED ARYLOXYALKYL DIAMINES

CROSS-REFERENCE TO RELATED APPLICATIONS

This application is a divisional of application Ser. No. 08/612,849, filed on Feb. 5, 1996, now U.S. Pat. No. 5,677,310, which in turn was the national stage of PCT Application Serial No. PCT/EP 94/02702, filed Aug. 12, 1994, which claims priority from European Patent Application Serial No. 93.202.445.8, filed on Aug. 19, 1993; and European Patent Application Serial No. 93.202.444.1, filed on Aug. 19, 1993.

The present invention relates to novel substituted aryloxy-alkyldiamine derivatives, processes for their preparations, pharmaceutical compositions containing them and their use as a medicine, in particular for the prevention and/or treatment of disorders characterized by excessive vasodilatation, especially migraine.

Migraine is a non-lethal disease suffered by one in ten individuals. The main symptom is headache; other symptoms include vomiting and photophobia. For many years the most widely used treatment for migraine involved the administration of ergotalkaloids, which show however several adverse side effects. Recently a tryptamine derivative, i.e. sumatriptan, was introduced as a novel antimigraine drug. We have now surprisingly found that the present novel substituted aryloxyalkyl diamine derivatives show 5-$HT_1$-like agonistic activity and can thus be used in the treatment of disorders characterized by excessive vasodilatation, especially migraine.

In Arzneimittel-Forschung, 25, 1404 (1975) some guanidine and amidine derivatives, among which N-[2-[2-(2-methoxyphenoxy)ethylamino]ethyl]guanidine, are disclosed as having noradrenaline depleting activity.

In EP-0,511,072 derivatives of 2-aminopyrimidine-4-carboxamide having the general formula (A) are disclosed as antagonists of $\alpha_1$-adrenergic receptors.

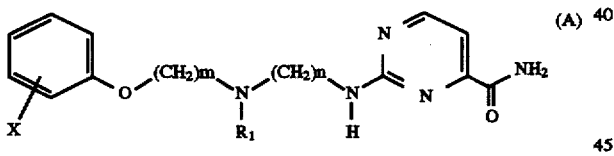

(A)

The present invention is concerned with compounds having the formula

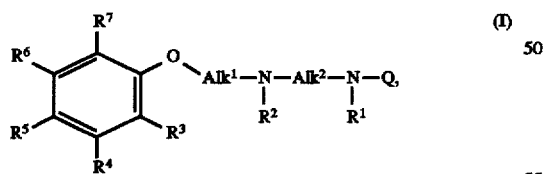

(I)

the pharmaceutically acceptable acid addition salts thereof, and the stereochemically isomeric forms thereof, wherein
$R^1$ and $R^2$ each independently are hydrogen or $C_{1-6}$alkyl;
$R^3$ is $C_{1-6}$alkyl, hydroxy, cyano, halo, $C_{1-6}$alkyloxy, aryloxy, arylmethoxy, $C_{2-6}$alkenyl, $C_{2-6}$alkynyl, $C_{1-6}$alkyl—S—, $C_{1-6}$alkyl(S=O)—, $C_{1-6}$alkylcarbonyl;
$R^4$ is hydrogen, halo, hydroxy, $C_{1-6}$alkyl, or $C_{1-6}$alkyloxy; or
$R^3$ and $R^4$ taken together form a bivalent radical of formula —CH=CH—CH=CH— (a),
—(CH$_2$)$_n$— (b),
—(CH$_2$)$_m$—X— (c),
—X—(CH$_2$)$_m$— (d),
—CH=CH—X— (e),
—X—CH=CH— (f),
—O—(CH$_2$)$_t$—Y— (g),
—Y—(CH$_2$)$_t$—O— (h),
—(CH$_2$)$_t$—Z— (i),
—Z—(CH$_2$)$_t$— (j), in these bivalent radicals one or two hydrogen atoms may be substituted with
$C_{1-6}$alkyl, $C_{1-6}$alkylcarbonyl or $C_{1-6}$alkyl—S(O)—;
each X independently is —O—, —S—, —S(O)—, —S(O)$_2$—, —C(O)—, —NR$^8$—;
n is 3 or 4;
each Y independently is —O—, —S—, —S(O)—, —S(O)$_2$—, —C(O)—, —NR$^8$—;
m is 2 or 3;
each Z is —O—C(O)—, —C(O)—O—, —NH—C(O)—, —C(O)—NH—, —O—S(O)$_2$—;
t is 1 or 2;
$R^8$ is hydrogen, $C_{1-6}$alkyl, $C_{1-6}$alkylcarbonyl or $C_{1-6}$alkyl—S(O)—;
$R^5$ and $R^6$ each independently are hydrogen, halo, hydroxy, $C_{1-6}$alkyl, $C_{1-6}$alkyloxy, aryloxy or arylmethoxy;
$R^7$ is hydrogen;
Alk$^1$ is $C_{2-5}$alkanediyl;
Alk$^2$ is $C_{2-15}$alkanediyl;
Q is a radical of formula

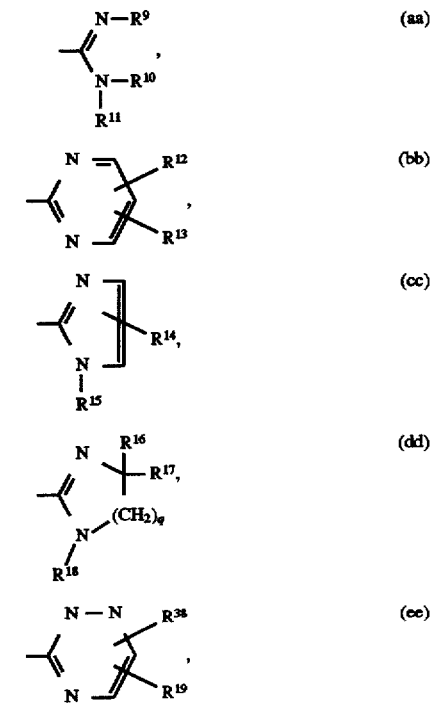

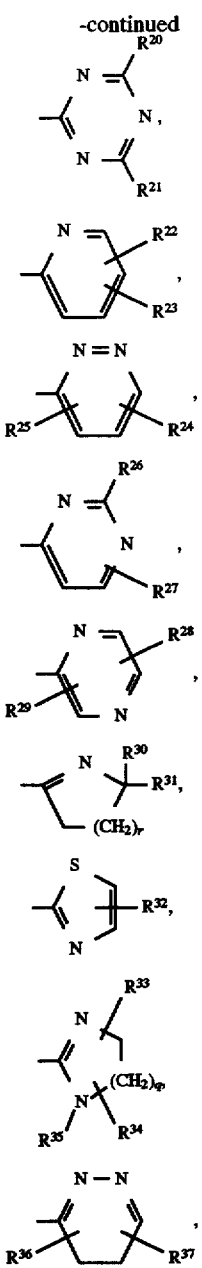

wherein
R⁹ is hydrogen, cyano, aminocarbonyl or $C_{1-6}$alkyl;
R¹⁰ is hydrogen, $C_{1-6}$alkyl, $C_{3-6}$alkenyl, $C_{3-6}$alkynyl, $C_{3-6}$cycloalkyl or aryl$C_{1-6}$alkyl;
R¹¹ is hydrogen or $C_{1-6}$alkyl; or
R¹⁰ and R¹¹ taken together may form a bivalent radical of formula —$(CH_2)_4$— or —$(CH_2)_5$—, or a piperazine which is optionally substituted with $C_{1-6}$alkyl;
R¹², R¹³, R¹⁴, R¹⁹, R²⁰, R²¹, R²², R²³, R²⁴, R²⁵, R²⁶, R²⁷, R²⁸, R²⁹, R³⁶, R³⁷ and R³⁸ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)—amino, aminocarbonyl, $C_{1-6}$alkyloxycarbonylamino, $C_{1-6}$alkylaminocarbonylamino, piperidinyl, pyrrolidinyl;
R¹⁵, R¹⁸ and R³⁵ each independently are hydrogen, $C_{1-6}$alkyl, $C_{1-6}$alkylcarbonyl, or aryl$C_{1-6}$alkyl;
q is 1, 2 or 3;
R¹⁶ and R¹⁷ are both hydrogen, or taken together with the carbon atom to which they are connected form C(O);
r is 1, 2 or 3;
R³⁰ and R³¹ are both hydrogen or taken together with the carbon atom to which they are connected form C(O);
R³² is hydrogen, halo or $C_{1-6}$alkyl;
R³³ is hydrogen and R³⁴ is hydroxy; or R³³ and R³⁴ taken together may form a bivalent radical of formula $(CH_2)_3$ or $(CH_2)_4$ which is optionally substituted with $C_{1-6}$alkyl; and aryl is phenyl optionally substituted hydroxy, halo, $C_{1-6}$alkyl, $C_{1-6}$alkyloxy.

All the compounds of formula (I) are deemed novel except for (a) N-[2-[2-(2-methoxyphenoxy)ethylamino]ethyl] guanidine; and (b) the compounds of formula (I) wherein R³ is methoxy, ethoxy or isopropyl; R⁴ is hydrogen; R⁵ is hydrogen; R⁶ is chloro, fluoro or methyl; R⁷ is hydrogen; R² is hydrogen or methyl; R¹ is hydrogen; Alk¹ is 1,2-ethanediyl or 1,3-propanediyl; ALk² is 1,2-ethanediyl or 1,3-propanediyl; Q is a radical of formula (bb), wherein R¹² is hydrogen and R¹³ is 4-aminocarbonyl.

Some of the compounds of formula (I) may also exist in their tautomeric forms. Such forms although not explicitly indicated in the above formula are intended to be included within the scope of the present invention.

As used in the foregoing definitions halo defines fluoro, chloro, bromo and iodo; $C_{1-6}$alkyl defines straight and branch chained saturated hydrocarbon radicals having from 1 to 6 carbon atoms such as, for example, methyl, ethyl, propyl, butyl, pentyl, hexyl as well as the branched isomers thereof; $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated, $C_{2-6}$alkenyl defines $C_{3-6}$alkenyl and the lower homologue thereof, i.e. ethenyl; $C_{3-6}$alkynyl defines straight and branch chained hydrocarbon radicals containing one triple bond and having from 3 to 6 carbon atoms such as, for example, 2-propynyl, 3-butynyl, 2-butynyl, 2-pentynyl, 3-pentynyl, 3-hexynyl, and the like; and the carbon atom of said $C_{3-6}$alkynyl radical being connected to a nitrogen atom preferably is saturated; $C_{2-6}$alkynyl defines $C_{3-6}$alkynyl and the lower homologue thereof, i.e. ethynyl; $C_{3-6}$cycloalkyl is generic to cyclopropyl, cyclobutyl, cyclopentyl and cyclohexyl; $C_{2-5}$alkanediyl defines bivalent straight and branch chained saturated hydrocarbon radicals having form 2 to 5 carbon atoms such as, for example, 1,2-ethanediyl, 1,3-propanediyl, 1,4-butanediyl, 1,5-pentanediyl and the like; $C_{2-15}$alkanediyl defines bivalent straight and branch chained saturated hydrocarbon radicals having from 2 to 15 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl, and the branched isomers thereof. The term "C(O)" refers to a carbonyl group.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term addition salt also comprises the hydrates and solvent addition forms which the compounds of formula (I) are able to form. Examples of such forms are e.g. hydrates, alcoholates and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; $C_{2-6}$-alkenyl radicals may have the E- or Z-configuration. Stereochemically isomeric forms of the compounds of formula (I) are obviously intended to be embraced within the scope of this invention.

$R^1$ is suitably hydrogen or methyl, preferably $R^1$ is hydrogen;

$R^2$ is suitably hydrogen or methyl, preferably $R^2$ is hydrogen;

$R^3$ is suitably $C_{1-6}$alkyl, hydroxy, $C_{1-6}$alkyloxy, arylmethoxy, preferably $R^3$ is methyl, ethyl, hydroxy, methoxy, ethoxy or phenylmethoxy;

$R^4$ is suitably hydrogen, $C_{1-6}$alkyl or $C_{1-6}$alkyloxy, preferably $R^4$ is hydrogen or methoxy;

or when taken together $R^3$ and $R^4$ form suitably a bivalent radical for formula (a), (b), (e), (f), (g) or (h);

each X is suitably O or S, preferably each X is O;
each Y is suitably O or S, preferably each Y is O;
each Z is suitably —O—C(O)—, —C(O)—O—;
$R^8$ is suitably hydrogen or $C_{1-6}$alkyl; preferably
$R^8$ is hydrogen or methyl;
$R^5$ is suitably hydrogen or $C_{1-6}$alkyl, preferably $R^5$ is hydrogen or methyl;
$R^6$ is suitably hydrogen or $C_{1-6}$alkyl, preferably $R^6$ is hydrogen or methyl;
$Alk^1$ is suitably $C_{2-3}$alkanediyl, preferably $Alk^1$ is 1,2-ethanediyl, 1,2-propanediyl or 1,3-propanediyl;
$Alk^2$ is suitably $C_{2-6}$alkanediyl, preferably $Alk^2$ is 1,3-propanediyl or 1,4-butanediyl;
Q is preferably a radical of formula (aa), (bb) or (dd);
$R^9$ is suitably hydrogen, cyano, aminocarbonyl or methyl, preferably $R^9$ is hydrogen or cyano;
$R^{10}$ is suitably hydrogen or $C_{1-6}$alkyl, preferably $R^{10}$ is hydrogen, methyl or ethyl;
$R^{11}$ is suitably hydrogen or $C_{1-6}$alkyl, preferably $R^{11}$ is hydrogen or methyl;
$R^{12}$ and $R^{13}$ each independently are suitably hydrogen, hydroxy, halo or methyl, preferably both $R^{12}$ and $R^{13}$ are hydrogen or $R^{12}$ is hydrogen and $R^{13}$ is hydroxy;
$R^{14}$ is suitably hydrogen or hydroxy, preferably $R^{14}$ is hydrogen;
$R^{15}$ is suitably hydrogen or phenylmethyl, preferably $R^{15}$ is hydrogen;
q is preferably 2;
$R^{16}$ and $R^{17}$ is are both preferably hydrogen;

$R^{18}$ is suitably hydrogen or phenylmethyl, preferably $R^{18}$ is hydrogen;

$R^{19}$ is suitably hydrogen, halo or methyl, preferably $R^{19}$ is hydrogen or chloro;

$R^{20}$ and $R^{21}$ each independently suitably are hydrogen, halo or methyl, preferably $R^{20}$ and $R^{21}$ are hydrogen or chloro;

$R^{22}$ and $R^{23}$ each independently suitably are hydrogen, hydroxy, chloro or methyl, preferably $R^{22}$ and $R^{23}$ are both hydrogen or $R^{22}$ is hydrogen and $R^{23}$ is hydroxy;

$R^{24}$ and $R^{25}$ each independently suitably are hydrogen, hydroxy, halo or methyl, preferably $R^{24}$ and $R^{25}$ are both hydrogen or $R^{24}$ is hydrogen and $R^{25}$ is chloro;

$R^{26}$ and $R^{27}$ each independently suitably are hydrogen, halo, $C_{1-6}$alkyloxy, $C_{1-6}$alkylthio, amino, mono- or di($C_{1-6}$alkyl)amino; preferably $R^{26}$ is hydrogen, chloro, methylthio or amino and $R^{27}$ is hydrogen;

$R^{28}$ and $R^{29}$ each independently suitably are hydrogen, halo, $C_{1-6}$alkyl, preferably $R^{28}$ and $R^{29}$ are hydrogen or chloro;

r preferably is 2;
$R^{30}$ and $R^{31}$ both preferably are hydrogen;
$R^{32}$ is suitably hydrogen or methyl, preferably $R^{32}$ is hydrogen; and
aryl is preferably phenyl.

Special compounds of formula (I) are those compounds of formula (I) wherein wherein $R^3$ is $C_{1-6}$alkyl, hydroxy, $C_{1-6}$alkyloxy, aryloxy, arylmethoxy, $C_{2-6}$alkenyl, $C_{2-6}$alkynyl; one of $R^4$, $R^5$ and $R^6$ is hydrogen and the others each independently are hydrogen, halo, hydroxy, $C_{1-6}$alkyl, or $C_{1-6}$alkyloxy, Q is a radical of formula (aa), (bb), (cc), (dd), (ee) wherein $R^{38}$ is hydrogen, (ff), (gg), (hh), (ii), (jj), (kk), (ll).

Other special compounds of formula (I) are those compounds of formula (I) wherein $R^3$ and $R^4$ taken together form a bivalent radical of formula

| | |
|---|---|
| —CH=CH—CH=CH— | (a), |
| —(CH₂)ₙ— | (b), |
| —(CH₂)ₘ—X— | (c), |
| —X—(CH₂)ₘ— | (d), |
| —CH=CH—X— | (e), |
| —X—CH=CH— | (f), |
| —O—(CH₂)₂—Y— | (g), |
| —Y—(CH₂)₂—O— | (h), |
| —(CH₂)ₜ—Z— | (i), |
| —Z—(CH₂)ₜ— | (j), | in these bivalent radicals one or two hydrogen atoms may be substituted with $C_{1-6}$alkyl, $C_{1-6}$alkylcarbonyl or $C_{1-6}$alkylsulfoxyl; and wherein X, Y, Z, m, n, and t are defined as in claim 1; and Q is a radical of formula (aa), (bb), (cc), (dd), (ee) wherein $R^{38}$ is hydrogen, (ff), (gg), (hh), (ii), (jj), (kk), (ll).

Interesting compounds are those compounds of formula (I), wherein $R^1$ and $R^2$ both are hydrogen.

An interesting subset of compounds are those compounds of formula (I), wherein $R^3$ and $R^4$ taken together do not form a bivalent radical and wherein $R^3$ is $C_{1-6}$alkyl, hydroxy, $C_{1-6}$alkyloxy or arylmethoxy, especially methyl, hydroxy, methoxy, ethoxy and phenylmethoxy.

Further interesting compounds are those compounds of formula (I) wherein $R^4$ is hydrogen, $C_{1-6}$alkyl or $C_{1-6}$alkyloxy and $R^5$ is hydrogen or $C_{1-6}$alkyloxy.

Particular compounds are those compounds of formula (I) wherein Q is a radical of formula (aa), (bb) or (dd), especially (bb) or (dd).

Particularly interesting compounds are those interesting compounds, wherein Q is a radical of formula of (bb), wherein $R^9$ and $R^{10}$ are hydrogen.

Another group of particularly interesting compounds are those interesting compounds wherein Q is a radical of formula (dd), wherein q is 2, $R^{16}$ and $R^{17}$ are hydrogen and $R^{18}$ is hydrogen.

Another interesting subset of compounds are those compounds of formula (I), wherein $R^3$ and $R^4$ taken together form a bivalent radical of formula (a), (b), (e), (f), (g) or (h);

Particular compounds are those compounds of formula (I) wherein Q is a radical of formula (aa), (bb) or (dd), especially (bb) or (dd).

Particularly interesting compounds are those interesting compounds, wherein Q is a radical of formula (bb), wherein $R^{12}$ and $R^{13}$ are hydrogen.

Another group of particularly interesting compounds, wherein Q is a radical of formula (dd), wherein q is 2, $R^{15}$ and $R^{16}$ are hydrogen and $R^{17}$ is hydrogen.

Preferred compounds are:
N-[2-(2,3-dimethoxyphenoxy)ethyl]-N'-2-pyrimidinyl-1,3-propanediamine; 2-[2-[[3-(2-pyrimidinylamino)propyl]amino]ethoxy]phenol; N-[2-(2,3-dimethoxy- phenoxy)ethyl]-N'-(1,4,5,6-tetrahydro-2-pyrimidinyl)-1,3-propanediamine; N-[2-(2-methoxyphenoxy)ethyl]-N'-(1,4,5,6-tetrahydro-2-pyrimidinyl)-1,3-propane diamine; N-[2-(2-ethoxyphenoxy)ethyl]-N'-(1,4,5,6-tetrahydro-2-pyrimidinyl)- 1,3-propanediamine; N-[3-(2-methoxyphenoxy)propyl]-N'-( 1,4,5,6-tetrahydro-2-pyrimidinyl)-1,3-propanediamine; N-[2-[(2,3-dihydro-1,4-benzodioxin-5-yl)oxy]- ethyl]-N'-2-pyrimidinyl-1,3-propanediamine; N-[2-[(2,3-dihydro-1,4-benzodioxin-5-yl)-oxy]ethyl]-N'-(1,4,5,6-tetrahydro-2-pyrimidinyl)-1,3-propanediamine; N-[2-[(2,3-dihydro-1,4-benzodioxin-5-yl)oxy]ethyl]-N'-(1,4,5,6-tetrahydro-2- pyrimidinyl)-1,4-butanediamine; N-[2-(1-naphthalenyloxy)ethyl]- N'-(1,4,5, 6-tetrahydro-2-pyrimidinyl)-1,3-propanediamine, the pharmaceutically acceptable acid addition salt thereof or the stereochemically isomeric forms thereof.

The compounds of formula (I) can generally be prepared by reacting a diamine of formula (II) with a reagent of formula (III) wherein $W^1$ is a reactive leaving group such as, for example, halo, e.g. chloro, bromo; alkyloxy, e.g. methoxy, ethoxy and the like; aryloxy, e.g. phenoxy and the like; alkylthio, e.g. methylthio, ethylthio and the like; arylthio, e.g. benzenethio and the like.

In the formulas (II), (III) and all the following formulas the variables $R^1$, $R^2$, $R^3$, $R^4$, $R^5$, $R^6$, $R^7$, $Alk^1$, $Alk^2$, and Q are as defined under formula (I), unless indicated otherwise.

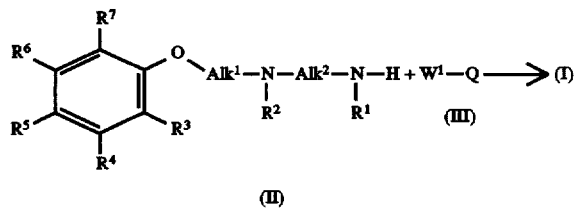

(II)

Said reaction can be performed by stirring the diamine of formula (II) with the reagent of formula (III) in an appropriate solvent such as, for example, an alcohol, e.g. ethanol and the like; a halogenated hydrocarbon, e.g. trichloromethane and the like or an ether, e.g. tetrahydrofuran and the like; an aromatic hydrocarbon, e.g. methylbenzene and the like; or mixtures thereof. Optionally a base such as, for example, an alkalimetal carbonate, e.g. sodium or potassium carbonate; an alkalimetal hydrogen carbonate, e.g. sodium or potassium hydrogen carbonate; an appropriate organic base, e.g. N,N-diethyl-ethanamine, pyridine and the like bases, can be added to pick up the acid that may be formed during the course of the reaction. Elevated temperatures may enhance the rate of the reaction. Preferably the reaction is performed at the reflux temperature of the reaction mixture.

The compounds of formula (I) can also generally be prepared by reductive N-alkylation of an aminoderivative of formula (VI) with an appropriate aldehyde of formula (V), wherein $Alk^3$ is $C_{1-4}$alkanediyl.

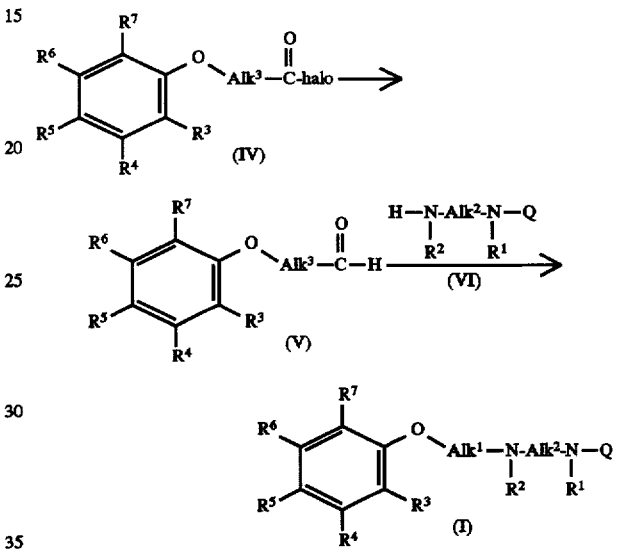

Said reaction is performed by stirring the reactants of formula (V) and (VI) in an appropriate solvent such as, for example, an alcohol, e.g. ethanol and the like; an ether, e.g. tetrahydrofuran and the like; an aromatic solvent, e.g. methylbenzene and the like, or mixtures thereof. Optionally a water separator can be used to remove the water that is formed during the course of the reaction. The resulting imine can then be reduced by reactive hydride reagents such as, for example, sodium borohydride, or by catalytic hydrogenation on an appropriate catalyst such as, for example, palladium on charcoal, platinum on charcoal, Raney nickel and the like in a suitable solvent such as, for example an alcohol, e.g. methanol, ethanol and the like; an ether, e.g. tetrahydrofuran and the like; a carboxylic ester, e.g. ethyl acetate, butyl acetate and the like; or a carboxylic acid, e.g. acetic acid, propanoic acid and the like. Optionally the reaction may be performed at elevated temperatures and/or pressures.

The intermediate aldehyde of formula (V) can be prepared by reducing an acyl derivative of formula (IV) wherein $Alk^3$ is defined as above. In turn said acyl halide can be prepared by reacting the corresponding, with a halogenating reagent such as thionylchloride, phosphorus trichloride, phosphorus tribromide, oxalylchloride and the like. The latter reaction may be performed in an excess of the halogenating reagent or in appropriate solvents such as, for example, halogenated hydrocarbons, e.g. dichloromethane, trichloromethane and the like; aromatic hydrocarbons, e.g. methyl-benzene and the like; ethers, e.g. tetrahydrofuran, 1,4-dioxane and the like, or dipolar aprotic solvents, e.g. N,N-dimethylformamide, N,N-dimethylacetamide and the like. Stirring and elevated temperatures may be appropriate to enhance the rate of the reaction.

Said reduction of the acylhalide of formula (IV) can for instance be performed by catalytic hydrogenation with a catalyst such as palladium on charcoal, palladium on bariumsulfate, platinum on charcoal and the like in appropriate solvents such as, for example, ethers, e.g. tetrahydrofuran and the like; preferably in admixture with a dipolar aprotic solvent such as, for example, N,N-dimethylformamide, N,N-dimethylacetamide and the like. Optionally a catalyst poison can be added such as thiophene, quinoline-sulfur and the like. The reaction sequence starting from the intermediate of formula (IV) and yielding compounds of formula (I) may be performed as a one-pot procedure.

The compounds of formula (I) can also be prepared by N-alkylating an amine of formula (VI) with an intermediate of formula (VII), wherein $W^2$ is a reactive leaving group such as, for example, halo, e.g. chloro, bromo or iodo; sulfonyloxy, e.g. methanesulfonyloxy, methylbenzenesulfonyloxy and the like, in appropriate solvents such as ketones, e.g. 2-butanone and the like; ethers, e.g. tetrahydrofuran and the like; aromatic hydrocarbons, e.g. methylbenzene and the like; dipolar aprotic solvents, e.g. N,N-dimethylformamide, N,N-dimethylacetamide, dimethylsulfoxide and the like.

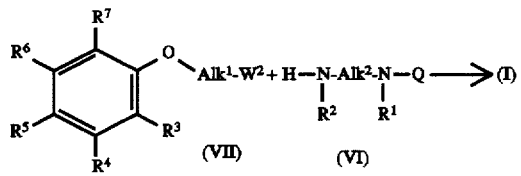

Stirring and heating may enhance the reaction rate. Optionally a suitable base may be added to pick up the acid that is formed during the course of the reaction such as, for example an alkali metal carbonate, e.g. sodium or potassium carbonate, an alkali metal hydrogen carbonate, e.g. sodium or potassium hydrogen carbonate and the like; an appropriate organic base, e.g. N,N-diethylethanamine, pyridine and the like.

The compounds of formula (I), can also be converted into each other by functional group transformations.

For instance the compounds of formula (I), wherein Q represents a pyrimidinyl moiety can be converted into their tetrahydroanalogs following art-known catalytic hydrogenation procedures.

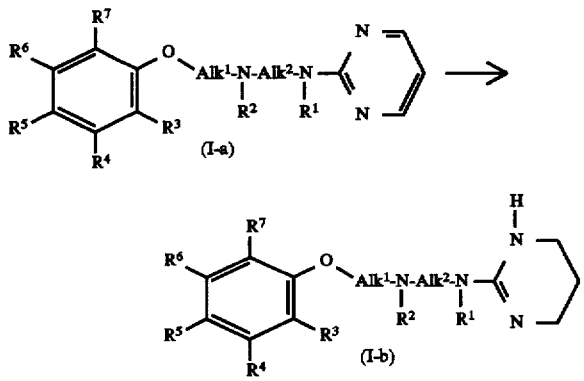

Furthermore, compounds of formula (I) bearing a $C_{2-6}$alkynylgroup or $C_{2-6}$alkenylgroup can be converted into the corresponding compounds bearing $C_{1-6}$alkylgroup following art-known hydrogenation techniques.

Compounds of formula (I) bearing a cyano group can be converted into the corresponding compounds bearing an aminomethyl substituent following art-known hydrogenation techniques.

Compounds bearing an alkyloxy substituent can be converted into compounds bearing a hydroxy group by treating the alkyloxy compound with an appropriate acidic reagent such as for example, hydrohalic acid, e.g. hydrobromic acid or borontribromide and the like.

Compounds bearing a arylmethoxy substituent may be converted into compounds bearing a hydroxy substituent following art-known debenzylation reactions such as, for example, hydrogenolysis.

Compounds bearing an amino substituent can be N-acylated or N-alkylated following art-known N-acylation or N-alkylation procedures.

Compounds bearing a thio-substituent may be oxidised to the corresponding sulfinyl derivatives.

Some of the intermediates mentioned hereinabove are art-known, others are novel and can be prepared following art-known methodologies.

Pure stereochemically isomeric forms of the compounds of this invention may be obtained by the application of art-known procedures. Diastereoisomers may be separated by physical separation methods such as selective crystallization and chromatographic techniques, e.g. liquid chromatography. Enantiomers may be separated from each other by the selective crystallization of their diastereomeric salts with optically active acids. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I), the pharmaceutically acceptable acid-addition salts and stereochemically isomeric forms thereof have interesting pharmacological properties: they show $5HT_{1-like}$ agonistic activity. The compounds of the present invention have remarkable vasoconstrictor activity. They are useful to treat conditions which are related to vasodilatation. For instance, they are useful in the treatment of conditions characterized by or associated with cephalic pain, e.g. cluster headache and headache associated with vascular disorders, especially migraine. These compounds are also useful in the treatment of venous insufficiency and in the treatment of conditions associated with hypotension.

The vasoconstrictor activity of the compounds of formula (I) can be determined using the test described in the pharmacological example, wherein the serotonin-like response of the compounds of the present invention was tested on the basilar arteries of pigs.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention therefore may be used as medicines in conditions related to vasodilatation, more in particular hypotension, venous insufficiency and especially cephalic pain among which especially migraine. The compounds of the present invention also provide a method of treating warm-blooded animals suffering from conditions related to vasodilatation such as, hypotension, venous insufficiency and especially cephalic pain among which migraine by administering an effective amount of a compound of formula (I), a pharmaceutically acceptable acid addition salt or a stereoisomeric form thereof. Those skilled in the art could easily determine the effective amount from the test results presented hereinafter. In general it is contemplated that an effective amount would be from 1 µg/kg to 1 mg/kg body weight, and in particular from 2 µg/kg to 200 µg/kg body weight. It may be appropriate to administer the required dose as two, three, four or more sub-doses at appropriate intervals throughout the day. Said sub-doses may be formulated as unit dosage forms, for example, containing 0.005 to 20 mg, and in particular 0.1 mg to 10 mg of active ingredient per unit dosage form.

The following examples are intended to illustrate and not to limit the scope of the present invention in all its aspects.

EXPERIMENTAL PART

A. Preparation of the Intermediates

Example 1 a) 2-bromo-1,1-diethoxyethane (0.097 mol) was added to a mixture of 2,3-dimethoxy-phenol (0.097 mol) and potassium carbonate (0.097 mol) in N,N-dimethylacetamide (200 ml). The reaction mixture was stirred for 24 hours at 140° C. The solvent was evaporated. The residue was partitioned between 1,1'-oxybisethane and a solution of NaOH in water. The organic layer was separated, washed with a saturated NaCl solution, dried (MgSO$_4$), filtered and the solvent was evaporated, yielding 23 g (87.7%) of 1-(2,2-diethoxyethoxy)-2,3-dimethoxybenzene (interm. 1).

b) Hydrochloric acid (2N) (125 ml) was added to a solution of intermediate (1) (0.078 mol) in 2-propanone (200 ml). The reaction mixture was stirred for 15 minutes at 60° C. The organic solvent was evaporated. Water (300 ml) was added. This mixture was extracted with 1,1'-oxybisethane (3×200 ml). The separated organic layer was washed with a saturated NaCl solution, dried (MgSO$_4$), filtered and the solvent was evaporated, yielding 11.6 g (76%) of 2-(2,3-dimethoxyphenoxy)acetaldehyde (interm.2).

In a similar manner were also prepared:
2-[2-(phenylmethoxy)phenoxy]acetaldehyde (interm. 3);
[2-(methylthio)phenoxy]acetaldehyde (interm. 4); and
[2-(methylsulfinyl)phenoxy]acetaldehyde (interm. 5).

Example 2

A mixture of N-[2-(2-methoxyphenoxy)ethyl] aminepropanenitrile (0.035 mol) in methanol (500 ml) was hydrogenated with Raney nickel (2 g) as a catalyst. After uptake of hydrogen (2 eq.), the catalyst was filtered off and the filtrate was evaporated, yielding 7.8 g (99.4%) of product. A sample (1.0 g) was dissolved in 2-propanol and converted into the hydrochloric acid salt (1:2). The salt was filtered off and dried, yielding 0.81 g (60.8%) of N-[2-(2-methoxyphenoxy)ethyl]-1,3-propanediamine dihydrochloride; mp. 149.4° C. (interm. 6).

Example 3 a) A mixture of 8-methoxy-1,2-benzoxathiin, 2,2-dioxide (0.020 mol) in a hydrobromic acid solution 48% in water (450 ml) was stirred and refluxed for 2 hours. The reaction mixture was cooled. The resulting precipitate was filtered off and the filtrate was extracted with diethyl ether. The separated organic layer was dried (MgSO$_4$), filtered and the solvent was evaporated, yielding: 37.4 g 1,2-benzoxathiin-8-ol, 2,2-dioxide (94.4%) (interm.7).

b) A mixture of intermediate 7 (0.13 mol), 2-bromoethanol (0.39 mol) and potassium carbonate (0.015 mol) in 2-propanone (50 ml) was stirred and refluxed overnight. The mixture was cooled and the resulting precipitate was filtered off. The filtrate was evaporated and the residue was crystallized from CH$_2$Cl$_2$. The precipitate was filtered off and the filtrate was evaporated. The residue was purified by column chromatography over silica gel (eluent: CH$_2$Cl$_2$/CH$_3$OH 97.5/2.5). The pure fractions were collected and the solvent was evaporated, yielding: 3.1 g (9.8%) of 2-(1,2-benzo- xathiin-8-yloxy)ethanol 2,2-dioxide (interm.8)

c) N,N,diethylethanamine (10 ml) was added dropwise to a mixture of intermediate 8 (0.089 mol) and methanesulfonyl chloride (0.13 mol) in 2-propanone (250 ml), stirred and cooled on an ice bath. The reaction mixture was stirred for 1 hour at room temperature. The mixture was filtered and the filtrate was evaporated. The residue was dissolved in CH$_2$Cl$_2$. The organic solution was washed with an aqueous hydrochloric acid solution, dried (MgSO$_4$), filtered and the solvent was evaporated. The residue was crystallized from CH$_2$Cl$_2$. The precipitate was filtered off and dried (vacuum; 70° C.), yielding 15.6 g (54.7%) 2-(1,2-benzoxathiin-8-yloxy)ethanol 2,2-dioxide methanesulfonate (ester); mp. 117° C. (interm.9).

d) A mixture of intermediate 9 (0.019 mol) in methanol (250 ml) was hydrogenated with palladium-on-charcoal catalyst (2 g) as a catalyst. After uptake of hydrogen (H₂) (1 equiv), the catalyst was filtered off and the filtrate was evaporated. The residue was crystallized from CH₃CN. The precipitate was filtered off and dried (vacuum; 60° C.), yielding: 3.1 g (50.6%) 2-[(3,4-dihydro-1,2-benzoxathiin-8-yl)oxy]ethanol methanesulfonate(ester) 2,2-dioxide; mp. 155° C. (interm.10)

Example 4 a) A mixture of 2,3-dihydro-5-hydroxy-1,4-benzodioxin (0.13 mol), 2-bromo- 1,1-diethoxyethane (0.13 mol) and potassium carbonate (0.13 mol) in N,N-dimethyl- acetamide (250 ml) was stirred overnight at 140° C. The solvent was evaporated. The residue was partitioned between 1,1'-oxybisethane and water. The organic layer was separated, washed with a saturated NaCl solution, dried (MgSO₄), filtered and the solvent was evaporated. The residual oil was crystallized from 2,2'-oxybispropane. The precipitate was filtered off and dried, yielding 21 g (60.2%) 5-(2, 2diethoxyethoxy)-2,3- dihydro-1,4-benzodioxin; mp. 73.1° C. (interm.11).

b) Hydrochloric acid 2N (125 ml) was added to a solution of intermediate (R 97.205) (0.078 mol) in 2-propanone (200 ml). The reaction mixture was stirred for 15 minutes at 60° C. The organic solvent was evaporated (40° C.). Water (300 ml) was added. This mixture was extracted with dichloromethane. The separated organic layer was dried (MgSO₄), filtered and the solvent was evaporated, yielding 13 g (86.6%) of [(2,3- dihydro-1,4-benzodioxin-5-yl)oxy] acetaldehyde (interm.12).

TABLE 1

In this manner were prepared:

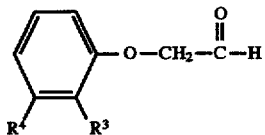

| Int. no. | R³, R⁴ |
|---|---|
| 12 | —O—(CH₂)₂—O— |
| 13 | —(CH₂)₄— |
| 14 | —O—CH=CH— |
| 15 | —O—(CH₂)₃— |
| 16 | —(CH₂)₃—O— |
| 17 | —C(CH₃)=C(CH₃)—O— |

B. Preparation of the Final Compounds

Example 5

A mixture of intermediate 6 (0.03 mol), 2-chloropyrimidine (0.03 mol) and sodium carbonate (0.03 mol) in ethanol (150 ml) was stirred and refluxed overnight. The reaction mixture was filtered over dicalite. The filtrate was evaporated. The residue was dissolved in acetonitrile and this mixture was acidified with HCl/2-propanol. The precipitate was filtered off. The filtrate was evaporated and the residue was stirred in water. This mixture was alkalized with NaOH, then extracted with 1,1'-oxybisethane. The separated organic layer was dried (MgSO₄), filtered and the solvent was evaporated. The residue was dissolved in warm methanol (500 ml) and converted into the ethanedioic acid salt (1:2) with a solution of ethanedioic acid (8 g) in methanol. The salt was filtered off and dried, yielding 6.8 g (56.3%) of N-[2-(2-methoxyphenoxy)ethyl]-N'-2-pyrimidinyl-1,3- propanediamine ethanedioate (1:2); mp. 178.4° C. (comp. 1).

Example 6

N-2-pyrimidinyl-1,3-propanediamine (0.042 mol) was added to a solution of intermediate 2 (0.056 mol) in ethanol (200 ml) and this mixture was stirred for 30 min. at room temperature. The reaction mixture was cooled to 0° C. with an ice salt bath. Sodium borohydride (0.059 mol) was added and the reaction mixture was stirred for 30 minutes at 0° C., then for 1 hour at room temperature. A small amount of water was added and the solvent was evaporated at 40° C. The residue was partitioned between dichloromethane and water. The organic layer was separated, dried (MgSO₄), filtered and the solvent was evaporated. The residual oil (13 g) was purified by column chromatography over silica gel (eluent: CH₂Cl₂/(CH₃OH/NH₃) 95/5). The desired fractions were collected and the solvent was evaporated. The residual oil(8 g) was dissolved in 2-propanone and converted into the ethanedioic acid salt (1:1). The precipitate was filtered off and crystallized from methanol. The precipitate was filtered off and dried, yielding 6.7 g (37.8%) of N-[2-(2,3-dimethoxyphenoxy)ethyl]-N'-2-pyrimidinyl-1,3-propanediamine ethanedioate(1:1); mp. 200.0° C. (comp. 2).

Example 7 a) A mixture of intermediate 3 (0.117 mol) and N-2-pyrimidinyl-1,3-propanediamine (0.087 mol) in ethanol (500 ml) was stirred for 45 minutes at 20° C. The reaction mixture was cooled to 0° C. (ice salt bath). Sodium borohydride (0.125 mol) was added in one portion and the reaction mixture was stirred for 2 hours. Water was added and the solvent was evaporated. The residue was partitioned between 1,1'-oxybisethane and water. The organic layer was separated, dried, filtered and the solvent was evaporated. The residue was purified by column chromatography over silica gel (eluent: CH₂Cl₂/ (CH₃OH/NH₃) 95/5). The pure fractions were collected and the solvent was evaporated. The residue was crystallized from 2-propanol. The precipitate was filtered off and dried, yielding 7.7 g (23.4%) of N-[2-[2-(phenylmethoxy)phenoxy]ethyl]-N'-2-pyrimidinyl- 1,3-propanediamine; mp. 90.1° C. (comp. 3).

b) A mixture of compound (97232) (0.02 mol) in methanol (250 ml) was hydrogenated with palladium on activated carbon 10% (2 g) as a catalyst. After uptake of hydrogen (1 eq.), the catalyst was filtered off. The filtrate was evaporated. The residue was dissolved in ethanol and converted into the hydrochloric acid salt (1:2) with HCl/ 2-propanol. The salt was filtered off and dried, yielding 4.8 g (66.4%) of 2-[2-[[3-(2-pyrimidinylamino)propyl]amino]ethoxy]phenol dihydrochloride; mp. 166.4° C. (comp. 4).

Example 8

A mixture of 1-bromo-3-(2-methoxyphenoxy)propane (0.020 mol), N-2-pyrimidinyl- 1,3-propanediamine (0.020 mol) and potassium carbonate (0.03 mol) in N,N-dimethylacetamide (50 ml) was stirred for 48 hours at 70° C. The solvent was evaporated. The residue was partitioned between dichloromethane and water. The oprganic layer was separated, dried (MgSO₄), filtered and the solvent was evaporated. The residual oil was purified by column chromatography over silica gel (eluent: CH₂Cl₂/(CH₃OH/NH₃) 95/5). The desired fractions were collected and the solvent was evaporated. The residue (5 g) was dissolved in 2-propanone and converted into the ethanedioic acid salt (1:1). The precipitate was filtered off and crystallized from methanol. The precipitate was filtered off and dried, yielding 3.41 g of product. This fraction was recrystallized from methanol. The precipitate was filtered off and dried, yielding 3.3 g (40.6%) N-[3-(2- methoxyphenoxy)propyl]-N'-2-pyrimidinyl-1,3-propanediamine ethanedioate(1:1); mp. 186.3° C. (comp. 5).

Example 9

A mixture of compound 2 (0.0135 mol) and ethanedioic acid dihydrate (0.0135 mol) in 2-methoxyethanol (300 ml) was hydrogenated at 80° C. with palladium on activated carbon 10% (2 g) as a catalyst in the presence of a 4% solution of thiophene (2 ml). After uptake of hydrogen (2 eq.), the catalyst was filtered off and the filtrate was evaporated. The residue was crystallized from methanol. The precipitate was filtered off and dried, yielding 2.56 g (36.7%) of N-[2-(2,3-dimethoxyphenoxy)ethyl]-N'-(1,4,5,6-tetrahydro- 2-pyrimidinyl)-1,3-propanediamine ethanedioate (1:2); mp. 181.1° C. (comp. 6).

Example 10

N-2-pyrimidinyl-1,3-propanediamine (0.05 mol) was added to a solution of intermediate 12 (0.067 mol) in ethanol (200 ml) and this mixture was stirred for 30 minutes at room temperature. The reaction mixture was cooled to 0° C. with an ice salt bath. Sodium borohydride (0.070 mol) was added and the reaction mixture was stirred for 30 minutes at 0° C., then for 30 minutes at room temperature. A small amount of water was added and the solvent was evaporated. The residue was partitioned between dichloromethane and water. The organic layer was separated, dried (MgSO$_4$), filtered and the solvent was evaporated. The residual oil was purified by column chromatography over silica gel (eluent: CH$_2$Cl$_2$/(CH$_3$OH/NH$_3$) 95/5). The desired fractions were collected and the solvent was evaporated. The residual oil was dissolved in 2-propanone and converted into the ethanedioic acid salt (1:2). The precipitate was filtered off and crystallized from methanol. The precipitate was filtered off and dried, yielding 6 g (23.5%) of N-[2-[(2,3- dihydro-1,4-benzodioxin-5-yl)oxy]ethyl]-N'-2-pyrimidinyl-1,3-propanediamine ethane- dioate (1:1); mp. 213.2° C. (comp. 7).

Example 11

A mixture of 5-(3-chloropropoxy)-2,3-dihydro-1,4-benzodioxin (0.017 mol), N-2-pyrimidinyl-1,3-propanediamine (0.026 mol) and calcium oxid (5 g) in tetrahydro-furan (150 ml) was stirred overnight at 160° C. (pressure vessel). The mixture was cooled, filtered and the filtrate was evaporated. The residue was purified by column chromatography over silica gel (eluent: CH$_2$Cl$_2$/(CH$_3$OH/NH$_3$) 95/5). The pure fractions were collected and the solvent was evaporated, yielding 2.66 g N-[3-[(2,3- dihydro-1,4-benzodioxin-5-yl)oxy]propyl]-N'-2-pyrimidinyl-1,3-propanediamine ethanedioate(1:1) (36.0%); mp. 200.2° C. (comp. 8)

Example 12

Compound 7 (0.0078 mol) and ethanedioic acid dihydrate (0.0078 mol) were dissolved in a warm mixture of 2-methoxyethanol (200 ml) and water (100 ml). This solution was hydrogenated at 80° C. with palladium on activated carbon (10%) (2 g) as a catalyst in the presence of a 4% thiophene solution (1 ml). After uptake of hydrogen (2 eq.), the catalyst was filtered off and the filtrate was evaporated. The residue was crystallized from methanol. The precipitate was filtered off and dried. This fraction was recrystallized from water. The precipitate was filtered off and dried, yielding 0.8 g of product. This fraction was recrystallized from methanol/water (5/1). The precipitate was filtered off and dried, yielding 0.5 g (13.7%) of N-[2-[(2,3-dihydro-1,4-benzodioxin-5- yl)oxy]ethyl]-N'-(1,4,5,6-tetrahydro-2-pyrimidinyl)-1,3-propanediamine ethanedioate(2:3); mp. 231.1° C. (comp. 9).

Example 13

[phenoxy-1-(1methylethyl)methylene]cyanamide (0.019 mol) was added to a solution of N-[(2,3-dihydro-1,4-benzodioxin-5-yl)oxy]ethyl]-1,4-propanediamine (0.019 mol) in methanol (100 ml). The reaction mixture was stirred for 4 days at room temperature. The solvent was evaporated. The resultant oil was purified by column chromatography over silica gel (eluent: CH$_2$Cl$_2$/CH$_3$OH 90/10). The pure fractions were collected and the solvent was evaporated. The resultant oil (2.9 g) was crystallized from CH$_3$CN. The precipitate was filtered off and dried, yielding: 2.4 g (34.9%) N"-cyano-N-[3-[[2-[(2,3- dihydro-1,4-benzodioxin-5-yl)oxy]ethyl]amino]propyl]-N'-(1-methylethyl)guanidine; mp. 120.6° C. (comp. 10).

Example 14

A mixture of compound 10 (0.003 mol) in hydrochloric acid in 2-propanol (10 ml) and methanol (50 ml) was stirred and refluxed for 30 minutes. The solvent was evaporated. The residue was crystallized from CH$_3$CN. The precipitate was filtered off and dried, yielding: 0.53 g (39.1%) of N-[[[3-[[2-[(2,3-dihydro-1,4-benzodioxin-5- yl)oxy]ethyl]amino]propyl]amino][(1-methylethyl)amino]methylene]urea dihydro- chloride; mp. 155.0° C. (comp.1 1).

In this manners were prepared:

TABLE 2

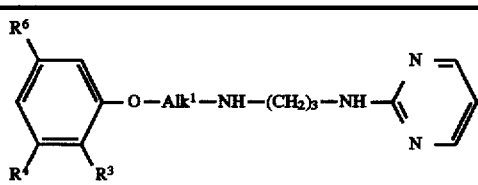

| Co. No. | Ex. No. | Alk$^1$ | R$^3$ | R$^4$, R$^6$ | physical data |
|---|---|---|---|---|---|
| 1 | 5 | (CH$_2$)$_2$ | O—CH$_3$ | H | mp. 178.4° C./.2 (COOH)$_2$ |
| 2 | 6 | (CH$_2$)$_2$ | O—CH$_3$ | 3-O—CH$_3$ | mp. 200.0° C./. (COOH)$_2$ |
| 3 | 7a | (CH$_2$)$_2$ | O—CH$_2$—C$_6$H$_5$ | H | mp. 90.1° C. |
| 4 | 7b | (CH$_2$)$_2$ | OH | H | mp. 166.4° C./.2 HCl |
| 5 | 8 | (CH$_2$)$_3$ | O—CH$_3$ | H | mp. 186.3° C./.(COOH)$_2$ |
| 12 | 6 | CH(CH$_3$)CH$_2$ | O—CH$_3$ | H | mp. 167.9° C./.2 HCl |
| 13 | 6 | (CH$_2$)$_2$ | CH$_3$ | H | mp. 204.8° C./. (COOH)$_2$ |
| 14 | 6 | (CH$_2$)$_2$ | O—CH$_2$—CH$_3$ | H | mp. 160.3° C./.2 (COOH)$_2$ |
| 15 | 6 | (CH$_2$)$_2$ | O—CH$_3$ | 5-CH$_3$ | mp. 197.2° C./. (COOH)$_2$ |
| 16 | 8 | (CH$_2$)$_2$ | CO—CH$_3$ | H | mp. 179.0° C./(COOH)$_2$ |
| 17 | 6 | (CH$_2$)$_2$ | S—CH$_3$ | H | mp. 217.6° C./(COOH)$_2$ |

TABLE 2-continued

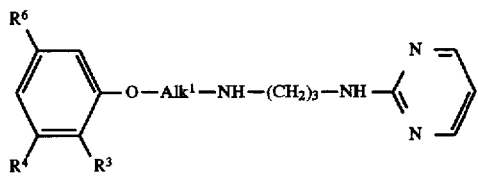

| Co. No. | Ex. No. | Alk¹ | R³ | R⁴, R⁶ | physical data |
|---|---|---|---|---|---|
| 18 | 8 | $(CH_2)_2$ | CN | H | mp. 185.1° C./(COOH)$_2$ |
| 19 | 6 | $(CH_2)_2$ | $SO-CH_3$ | H | mp. 177.7° C./2 (COOH)$_2$ |
| 20 | 8 | $(CH_2)_2$ | Br | H | mp. 198.2°/(COOH)$_2$ |

TABLE 3

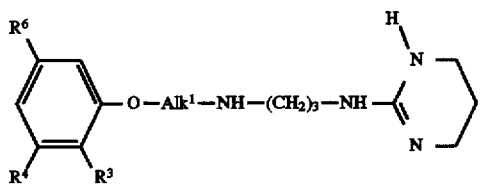

| Co. No. | Ex. No. | Alk¹ | R³ | R⁴, R⁶ | physical data |
|---|---|---|---|---|---|
| 6 | 9 | $(CH_2)_2$ | $O-CH_3$ | $3-O-CH_3$ | mp. 181.1° C./2 (COOH)$_2$ |
| 21 | 9 | $(CH_2)_2$ | $CH_3$ | H | mp. 170.3° C./2 HCl |
| 22 | 9 | $(CH_2)_2$ | $O-CH_3$ | H | mp. 159.1° C./2 (COOH)$_2$ |
| 23 | 9 | $(CH_2)_2$ | $O-CH_2-CH_3$ | H | mp. 168.1° C./2 (COCH)$_2$ |
| 24 | 9 | $(CH_2)_2$ | $O-CH_3$ | $5-CH_3$ | mp. 182.8° C./2 (COOH)$_2$ |
| 25 | 9 | $(CH_2)_2$ | OH | H | mp. 185.4° C./2 HCl |
| 26 | 9 | $(CH_2)_3$ | $O-CH_3$ | H | mp. 155.1° C./2 (COOH)$_2$ |
| 27 | 9 | $(CH_2)_2$ | $CO-CH_3$ | H | mp. 150.6° C./2 (COOH)$_2$ ½H$_2$O |
| 28 | 9 | $(CH_2)_2$ | CN | H | mp. 188.6° C./3/2 (COOH)$_2$ |

TABLE 4

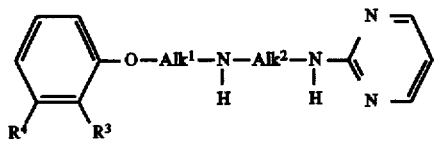

| Co. No. | Ex. No | R³, R⁴ | Alk¹ | Alk² | Physical data |
|---|---|---|---|---|---|
| 7 | 10 | $-O-(CH_2)_2-O-$ | $(CH_2)_2$ | $(CH_2)_3$ | mp. 213.2° C./. (COOH)$_2$ |
| 29 | 10 | $-O-(CH_2)_2-O-$ | $(CH_2)_2$ | $(CH_2)_4$ | mp. 210.1° C./. (COOH)$_2$ |
| 30 | 10 | $-O-(CH_2)_2-O-$ | $(CH_2)_2$ | $(CH_2)_2$ | mp. 204.1° C./. (COOH)$_2$ |
| 31 | 10 | $-CH=CH-CH=CH-$ | $(CH_2)_2$ | $(CH_2)_3$ | mp. 227.6° C./. (COOH)$_2$ |
| 32 | 10 | $-(CH_2)_4-$ | $(CH_2)_2$ | $(CH_2)_3$ | mp. 229.9° C./. (COOH)$_2$ |
| 33 | 10 | $-O-CH=CH-$ | $(CH_2)_2$ | $(CH_2)_3$ | mp. 223.3° C./. (COOH)$_2$ |
| 34 | 10 | $-O-(CH_2)_3-$ | $(CH_2)_2$ | $(CH_2)_3$ | mp. 206.6° C./. (COOH)$_2$ |
| 8 | 11 | $-O-(CH_2)_2-$ | $(CH_2)_3$ | $(CH_2)_3$ | mp. 200.0° C./. (COOH)$_2$ |
| 35 | 10 | $-S-CH=CH-$ | $(CH_2)_2$ | $(CH_2)_3$ | mp. 227.2° C./. (COOH)$_2$ |
| 36 | 10 | $-(CH_2)_3-O-$ | $(CH_2)_2$ | $(CH_2)_3$ | mp. 67.8° C. |
| 37 | 10 | $-(CH_2)_3-O-$ | $(CH_2)_2$ | $(CH_2)_3$ | mp. 219° C./. (COOH)$_2$ |
| 38 | 10 | $-C(CH_3)=C(CH_3)-O-$ | $(CH_2)_2$ | $(CH_2)_2$ | mp. 87.1° C. |
| 39 | 11 | $-C(CH_2)_2-S(O)_2-O-$ | $(CH_2)_2$ | $(CH_2)_2$ | mp. 207.5° C./. (COOH)$_2$ |

TABLE 5

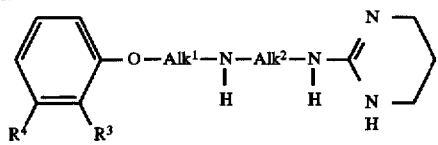

| Co. No. | Ex. No | $R^3, R^4$ | $Alk^1$ | $Alk^2$ | Physical data |
|---|---|---|---|---|---|
| 9 | 12 | $-O-(CH_2)_2-O-$ | $-(CH_2)_2-$ | $-(CH_2)_3-$ | mp. 231.1° C./.3/2 $(COOH)_2$ |
| 40 | 12 | $-O-(CH_2)_2-O-$ | $-(CH_2)_2-$ | $-(CH_2)_4-$ | mp. 193.7° C./.2 $(COOH)_2$ |
| 41 | 12 | $-O-(CH_2)_2-O-$ | $-(CH_2)_2-$ | $-(CH_2)_2-$ | mp. 213.5° C./.2 $(COOH)_2$ |
| 42 | 12 | $-CH=CH-CH=CH-$ | $-(CH_2)_2-$ | $-(CH_2)_3-$ | mp. 221.3° C./.2 $(COOH)_2$ |
| 43 | 12 | $-(CH_2)_4-$ | $-(CH_2)_2-$ | $-(CH_2)_3-$ | mp. 205.6° C./.2 $(COOH)_2$ |
| 44 | 12 | $-O-(CH_2)_3-$ | $-(CH_2)_2-$ | $-(CH_2)_3-$ | mp. 230.8° C./.3/2 $(COOH)_2$ |
| 45 | 12 | $-O-CH=CH-$ | $-(CH_2)_2-$ | $-(CH_2)_3-$ | $2(COOH)_2$ |
| 46 | 12 | $-O-(CH_2)_2-O-$ | $-(CH_2)_3-$ | $-(CH_2)_3-$ | mp. 205.5° C./.2 $(COOH)_2$ |
| 47 | 12 | $-(CH_2)_3-O-$ | $-(CH_2)_2-$ | $-(CH_2)_3-$ | mp. 191.1° C./.2 $(COOH)_2$ |
| 48 | 12 | $-C(CH_3)=C(CH_3)O-$ | $-(CH_2)_2-$ | $-(CH_2)_3-$ | mp. 194.0° C./.2 $(COOH)_2$ |

TABLE 6

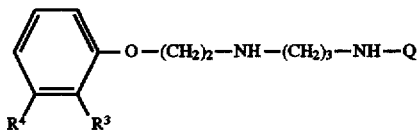

| Co. No. | Ex. No. | $R^3, R^4$ | Q | physical data |
|---|---|---|---|---|
| 10 | 13 | $-O-(CH_2)_2-O-$ | $\underset{\overset{\|}{NH-CH(CH_3)_2}}{N-CN}$ | mp. 181.1° C./.2 $(COOH)_2$ |
| 11 | 14 | $-O-(CH_2)_2-O-$ | $\underset{\overset{\|}{NH-CH(CH_3)_2}}{\overset{O}{\underset{\|}{N-C-NH_2}}}$ | mp. 155.0° C./.2 HCl |

C. Pharmacological Example

Example 15

Segments of basilar arteries taken from pigs (anaesthetised with sodium pentobarbital) were mounted for recording of isometric tension in organ baths. The preparations were bathed in Krebs-Henseleit solution. The solution was kept at 37° C. and gassed with a mixture of 95% $O_2$–5% $CO_2$. The preparations were stretched until a stable basal tension of 2 grams was obtained.

The preparations were made to constrict with serotonin ($3 \times 10^{-7}$ M). The response to the addition of serotonin was measured and subsequently the serotonin was washed away. This procedure was repeated until stable responses were obtained.

Subsequently the test compound was administered to the organ bath and the constriction of the preparation was measured. This constrictive response was expressed as a percentage of the response to serotonin as measured previously.

The lowest active concentration was defined as the concentration at which 50% of the response to serotonin is obtained.

In table 7 the lowest active concentration of compounds of formula (I) are presented.

TABLE 7

| Co. No. | lowest active concentration (M) |
|---|---|
| 1 | $1 \cdot 10^{-6}$ |
| 2 | $3 \cdot 10^{-7}$ |
| 4 | $1 \cdot 10^{-6}$ |
| 6 | $1 \cdot 10^{-6}$ |
| 7 | $3 \cdot 10^{-7}$ |
| 9 | $3 \cdot 10^{-8}$ |
| 10 | $3 \cdot 10^{-7}$ |
| 11 | $1 \cdot 10^{-7}$ |
| 16 | $1 \cdot 10^{-7}$ |
| 17 | $1 \cdot 10^{-6}$ |
| 18 | $1 \cdot 10^{-6}$ |
| 19 | $1 \cdot 10^{-6}$ |
| 20 | $1 \cdot 10^{-7}$ |
| 21 | $1 \cdot 10^{-6}$ |
| 22 | $1 \cdot 10^{-6}$ |
| 23 | $3 \cdot 10^{-7}$ |
| 25 | $1 \cdot 10^{-6}$ |
| 26 | $3 \cdot 10^{-7}$ |
| 27 | $1 \cdot 10^{-7}$ |
| 29 | $1 \cdot 10^{-6}$ |
| 31 | $3 \cdot 10^{-8}$ |
| 32 | $3 \cdot 10^{-7}$ |
| 35 | $3 \cdot 10^{-7}$ |
| 36 | $3 \cdot 10^{-8}$ |
| 38 | $1 \cdot 10^{-6}$ |
| 39 | $1 \cdot 10^{-6}$ |
| 40 | $3 \cdot 10^{-6}$ |

TABLE 7-continued

| Co. No. | lowest active concentration (M) |
|---|---|
| 44 | $1 \cdot 10^{-6}$ |
| 45 | $3 \cdot 10^{-7}$ |
| 47 | $1 \cdot 10^{-7}$ |
| 48 | $1 \cdot 10^{-6}$ |

D. Composition Examples

"Active ingredient" (A. I.) as used throughout these examples relates to a compound of formula (I), a pharmaceutically acceptable acid addition salt or a stereochemically isomeric form thereof.

Example 16: Oral Drops

500 Grams of the A. I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A. I. The resulting solution was filled into suitable containers.

Example 17: Oral Solution

9 Grams of methyl 4-hydroxybenzoate and 1 gram of propyl 4hydroxybenzoate were dissolved in 4 l of boiling purified water. In 3 l of this solution were dissolved first 10 grams of 2,3-dihydroxybutanedioic acid and thereafter 20 grams of the A. I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 18: Capsules

20 Grams of the A. I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example 19: Film-Coated Tablets

Preparation of tablet core

A mixture of 100 grams of the A. I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 20: Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A. I. The solution was cooled to room temperature and supplemented with water for injection q.s. ad 1 l, giving a solution comprising 4 mg/ml of A. I. The solution was sterilized by filtration (U.S.P. XVII p. 811) and filled in sterile containers.

Example 21: Suppositories

3 Grams A. I. was dissolved in a solution of 3 grams 2,3-dihydroxybutanedioic acid in 25 ml polyethylene glycol 400. 12 Grams surfactant (SPAN®) and triglycerides (Witepsol 555®) q.s. ad 300 grams were molten together. The latter mixture was mixed well with the former solution. The thus obtained mixture was poured into moulds at a temperature of 37°–38° C. to form 100 suppositories each containing 30 mg/ml of the A. I.

Example 22: Injectable Solution

60 Grams of A. I. and 12 grams of benzylalcohol were mixed well and sesame oil was added q.s. ad 1 l, giving a solution comprising 60 mg/ml of A. I. The solution was sterilized and filled in sterile containers.

We claim:

1. A compound of the formula:

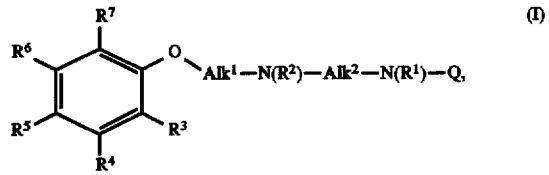

the pharmaceutically acceptable acid addition salts thereof, and the stereochemically isomeric forms thereof, wherein:

$R^1$ and $R^2$ each independently are hydrogen or $C_{1-6}$alkyl;

$R^3$ is $C_{1-6}$alkyl, hydroxy, cyano, halo, $C_{1-6}$alkyloxy, aryloxy, arylmethoxy, $C_{2-6}$alkenyl, $C_{2-6}$alkynyl, $C_{1-6}$alkyl—S—, $C_{1-6}$alkyl(S=O)—, $C_{1-6}$alkylcarbonyl;

$R^4$ is hydrogen, halo, hydroxy, $C_{1-6}$alkyl, or $C_{1-6}$alkyloxy; or $R^3$ and $R^4$ taken together form a bivalent radical of the formula:

| | |
|---|---|
| —CH=CH—CH=CH— | (a), |
| —(CH$_2$)$_n$— | (b), |
| —(CH$_2$)$_m$—X— | (c), |
| —X—(CH$_2$)$_m$— | (d), |
| —CH=CH—X— | (e), |
| —X—CH=CH— | (f), |
| —O—(CH$_2$)$_r$—Y— | (g), |
| —Y—(CH$_2$)$_r$—O— | (h), |
| —(CH$_2$)$_r$—Z— | (i), |

—Z—(CH₂)ₜ—  (j), wherein:
in the bivalent radicals (a) through (j) one or two hydrogen atoms may be substituted with $C_{1-6}$alkyl, $C_{1-6}$alkylcarbonyl or $C_{1-6}$alkyl—S(O)—;
each X independently is —O—, —S—, —S(O)—, —S(O)₂—, —C(O)—, or —NR⁸—;
n is 3 or 4;
each Y independently is —O—, —S—, —S(O)—, —S(O)₂—, —C(O)—, or —NR8—;
m is 2 or 3;
each Z independently is —O—C(O)—, —C(O)—O—, —NH—C(O)—, —C(O)—NH—, or —O—S(O)₂—;
t is 1 or 2; and
$R^8$ is hydrogen, $C_{1-6}$alkyl, $C_{1-6}$alkylcarbonyl or $C_{1-6}$alkyl—S(O)—;
$R^5$ and $R^6$ each independently are hydrogen, halo, hydroxy, $C_{1-6}$alkyl, $C_{1-6}$alkyloxy, aryloxy or arylmethoxy;
$R^7$ is hydrogen;
$Alk^1$ is $C_{2-5}$alkanediyl;
$Alk^2$ is $C_{2-15}$alkanediyl; and
Q is a radical of the formula:

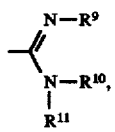

(aa)

wherein:
$R^9$ is hydrogen, cyano, aminocarbonyl or $C_{1-6}$alkyl;
$R^{10}$ is hydrogen, $C_{1-6}$alkyl, $C_{3-6}$alkenyl, $C_{3-6}$alkynyl, $C_{3-6}$cycloalkyl or aryl$C_{1-6}$alkyl;
$R^{11}$ is hydrogen or $C_{1-6}$alkyl;
or
$R^{10}$ and $R^{11}$ taken together may form a bivalent radical of the formula —(CH₂)₄— or —(CH₂)₅—, or a piperazine which is optionally substituted with $C_{1-6}$alkyl; and
aryl is phenyl, optionally substituted with hydroxy, halo, $C_{1-6}$alkyl, $C_{1-6}$alkyloxy;
with the proviso that N-[2-[2-(2-methoxyphenoxy)ethylamino]-ethyl]guanidine is excluded.

2. A compound as claimed in claim 1 wherein $R^3$ is $C_{1-6}$alkyl, hydroxy, $C_{1-6}$alkyloxy, aryloxy, arylmethoxy, $C_{2-6}$alkenyl, $C_{2-6}$alkynyl; and one of $R^4$, $R^5$ and $R^6$ is hydrogen and the others each independently are hydrogen, halo, hydroxy, $C_{1-6}$alkyl, or $C_{1-6}$alkyloxy.

3. A compound as claimed in claim 1 wherein $R^3$ and $R^4$ taken together form a bivalent radical of the formula:

—CH=CH—CH=CH—  (a),
—(CH₂)ₙ—  (b),
—(CH₂)ₘ—X—  (c),
—X—(CH₂)ₘ—  (d),
—CH=CH—X—  (e),
—X—CH=CH—  (f),
—O—(CH₂)ₜ—Y—  (g),
—Y—(CH₂)ₜ—O—  (h),
—(CH₂)ₜ—Z—  (i),
—Z—(CH₂)ₜ—  (j), in these bivalent radicals one or two hydrogen atoms may be substituted with $C_{1-6}$alkyl, $C_{1-6}$alkylcarbonyl or $C_{1-6}$alkylsulfoxyl; X, Y, Z, m and n are defined as in claim 11; and in the bivalent radicals of formula (g) and (h), t is 1 or 2.

4. A compound as claimed in claim 1 wherein $R^1$ and $R^2$ are hydrogen.

5. A compound according to claim 1 wherein the compound is:
N"-cyano-N-[3-[[2-[(2,3-dihydro-1,4-benzodioxin-5-yl)oxy]-ethyl]amino]propyl]-N'-(1-methylethyl)guanidine;
N-[[[3-[[2-[(2,3-dihydro-1,4-benzodioxin-5-yl)oxy]ethyl]amino]-propyl]amino][(1-methylethyl)amino]methylene]urea;
or a pharmaceutically acceptable acid addition salt thereof.

6. A pharmaceutical composition comprising a pharmaceutically acceptable carrier and as an active ingredient a therapeutically effective amount of a compound as claimed in claim 1.

7. A method for inducing vasoconstriction which comprises administering to a patient in need of the same an effective vasoconstriction amount of a compound of the formula:

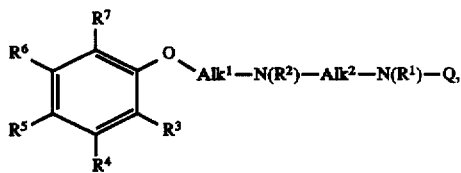

(I)

the pharmaceutically acceptable acid addition salts thereof, and the stereochemically isomeric forms thereof, wherein:
$R^1$ and $R^2$ each independently are hydrogen or $C_{1-6}$alkyl;
$R^3$ is $C_{1-6}$alkyl, hydroxy, cyano, halo, $C_{1-6}$alkyloxy, aryloxy, arylmethoxy, $C_{2-6}$alkenyl, $C_{2-6}$alkynyl, $C_{1-6}$alkyl—S—, $C_{1-6}$alkyl(S=O)—, $C_{1-6}$alkylcarbonyl;
$R^4$ is hydrogen, halo, hydroxy, $C_{1-6}$alkyl, or $C_{1-6}$alkyloxy;
or
$R^3$ and $R^4$ taken together form a bivalent radical of the formula:

—CH=CH—CH=CH—  (a),
—(CH₂)ₙ—  (b),
—(CH₂)ₘ—X—  (c),
—X—(CH₂)ₘ—  (d),
—CH=CH—X—  (e),
—X—CH=CH—  (f),
—O—(CH₂)ₜ—Y—  (g),
—Y—(CH₂)ₜ—O—  (h),
—(CH₂)ₜ—Z—  (i),
—Z—(CH₂)ₜ—  (j), wherein:

in the bivalent radicals (a) through (j) one or two hydrogen atoms may be substituted with $C_{1-6}$alkyl, $C_{1-6}$alkylcarbonyl or $C_{1-6}$alkyl—S(O)—;

each X independently is —O—, —S—, —S(O)—, —S(O)$_2$—, —C(O)—, or —NR$^8$—;

n is 3 or 4;

each Y independently is —O—, —S—, —S(O)—, —S(O)$_2$—, —C(O)—, or —NR$^8$—;

m is 2 or 3;

each Z independently is —O—C(O)—, —C(O)—O—, —NH—C(O)—, —C(O)—NH—, or —O—S(O)$_2$—;

t is 1 or 2; and

R$^8$ is hydrogen, $C_{1-6}$alkyl, $C_{1-6}$alkylcarbonyl or $C_{1-6}$alkyl—S(O)—;

R$^5$ and R$^6$ each independently are hydrogen, halo, hydroxy, $C_{1-6}$alkyl, $C_{1-6}$alkyloxy, aryloxy or arylmethoxy;

R$^7$ is hydrogen;

Alk$^1$ is $C_{2-5}$alkanediyl;

Alk$^2$ is $C_{2-15}$alkanediyl; and

Q is a radical of the formula:

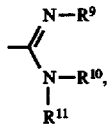 (aa)

wherein:

R$^9$ is hydrogen, cyano, aminocarbonyl or $C_{1-6}$alkyl;

R$^{10}$ is hydrogen, $C_{1-6}$alkyl, $C_{3-6}$alkenyl, $C_{3-6}$alkynyl, $C_{3-6}$cycloalkyl or aryl$C_{1-6}$alkyl; and R$^{11}$ is hydrogen or $C_{1-6}$alkyl;

or

R$^{10}$ and R$^{11}$ taken together may form a bivalent radical of the formula —(CH$_2$)$_4$— or —(CH$_2$)$_5$—, or a piperazine which is optionally substituted with $C_{1-6}$alkyl; and aryl is phenyl, optionally substituted with hydroxy, halo, $C_{1-6}$alkyl, $C_{1-6}$alkyloxy.

8. The method of claim 7 wherein said method comprises a method for treating migraine.

9. The method of claim 7 wherein said method comprises a method for treating hypotension.

10. The method of claim 7 wherein said method comprises a method for treating venous insufficiency.

* * * * *